United States Patent [19]

Romero-Sierra et al.

[11] 4,349,459

[45] Sep. 14, 1982

[54] LOWER PRESERVATION

[75] Inventors: Cesar Romero-Sierra, Bath; John C. Webb, Kingston, both of Canada

[73] Assignee: Queen's University at Kingston, Kingston, Canada

[21] Appl. No.: 243,465

[22] Filed: Mar. 13, 1981

Related U.S. Application Data

[63] Continuation-in-part of Ser. No. 45,126, Jun. 4, 1979, Pat. No. 4,272,571, which is a continuation-in-part of Ser. No. 914,172, Jun. 9, 1978, abandoned.

[51] Int. Cl.$^3$ .............................................. C09K 15/32
[52] U.S. Cl. ................................ 252/400 R; 252/404; 252/405; 252/406; 252/407; 71/68; 47/DIG. 2; 47/DIG. 11
[58] Field of Search ................... 252/400 R, 405, 404, 252/407, 406; 428/22, 24; 427/4; 71/68; 47/DIG. 2, DIG. 11

[56] References Cited

U.S. PATENT DOCUMENTS

| | | | |
|---|---|---|---|
| 2,658,836 | 10/1953 | Fessenden | 427/4 |
| 2,658,929 | 10/1953 | Ladd et al. | 570/189 |
| 2,971,292 | 2/1961 | Malecki | 47/58 |
| 4,272,571 | 6/1981 | Sierra et al. | 428/24 |

*Primary Examiner*—Joseph L. Schofer
*Assistant Examiner*—J. L. Barr
*Attorney, Agent, or Firm*—Richard J. Hicks; Stanley E. Johnson

[57] ABSTRACT

A relatively inexpensive solution for the single step preservation of fresh naturally colored blooms, comprising (in amounts per liter)

600–700 ml tert-butyl alcohol
200–250 ml 2-propanol
3–30 g thiourea
3–30 g citric acid
3–30 g sodium citrate
50–150 ml propionic acid
0–250 ml phenol.

3 Claims, No Drawings

LOWER PRESERVATION

This application is a continuation-in-part of our earlier filed application Ser. No. 045,126 filed June 4, 1979 and now allowed U.S. Pat. No. 4,272,571 and which in turn is a continuation-in-part of application Ser. No. 914,172 filed June 9, 1978 and now abandoned.

This application relates generally to the preservation of flowers and more particularly to a process and novel composition of matter for the preservation of the natural colours of flowers, and to the preserved flower product.

The preservation of flowers for museum specimens, for educational purposes in the natural sciences and elsewhere, for decorative and ornamental use, for displays and the like has been practised for many years and many processes for such preservation have been described in the literature. Attention is particularly directed to U.S. Pat. Nos. 2,658,929; 2,658,836 and 3,698,809 to Fessenden and U.S. Pat. No. 2,971,292 to Malecki and to "Handbook of Plastic Embedding" E. L. Lutz (1969) P. 60–73 for descriptions of the processes employed heretofore for the preservation of flowers and other plant and animal tissues. Such prior art processes are not, however, entirely satisfactory because the delicate natural colours of the flowers tend to fade relatively quickly and the flowers are also extremely brittle, fragile and highly susceptible to damage in extremes of temperature or humidity so that special handling and storage techniques are necessary. Without such special techniques the natural beauty of the flowers is quickly lost and the flowers lose their usefulness for display or educational purposes. Indeed, storage in sealed bells or embedding in plastic have heretofore been the only practical methods of storage and handling. Further, in order to treat differently coloured flowers according to the prior art it has been found necessary to use a variety of treatment solutions as no single treatment solution which is suitable for all colours of flowers, has evolved.

It is, therefore, an object of the present invention to provide a process and a single composition of matter for the preservation of flowers which is suitable for use with substantially all colours and varieties of flowers and which will result in naturally coloured flowers which retain the freshness, flexibility and beauty for relatively long periods of time without the necessity of special handling and storage techniques.

In application Ser. No. 045,126, now U.S. Pat. No. 4,272,571, the disclosure of which is incorporated herein by reference, we have disclosed essentially water free compositions, for the single step preservation of fresh, naturally coloured blooms, comprising at least one dehydrating alcohol, a urea-containing compound, a carboxylic acid, an alkaline citrate, an effective amount of at least one of: aluminum or magnesium sulphate, a transitional metal sulphate and an alkaline formaldehyde sulfoxylate, and zero to an effective amount of at least one of a silicone fluid and a silicone resin and which also contains a sufficient quantity of at least one compound of the group consisting of an alkaline phosphate, a lower carboxylic acid and phenol so as to ensure that the composition has a pH in the range 5 to 7.

A preferred composition within the above general formula comprises, in amounts per liter:
  175–575 ml. tertiary butyl alcohol
  100–300 ml. 1-propanol
  200–400 ml. 2-propanol
  6–8 g. sodium phosphate
  0–3 g. sodium formaldehyde sulfoxylate
  2.5–7.5 g. citric acid
  10–20 g. thiourea
  0–10 g. aluminum sulphate
  3–12 g. sodium citrate
  0–2 g. cupric sulphate
  10–200 ml. silicone fluid
  0–50 ml. silicone resin, and
  0–62 ml. phenol (88%).

Such formulations are effective for substantially all coloured blooms but have the disadvantage that they are relatively costly to prepare. We have now found that surprising good results may be obtained using generally similar solutions which are very much cheaper to prepare.

By one aspect of the present invention there is provided a composition for the single step preservation of fresh, naturally coloured blooms comprising (in amounts per liter of solution):
  600–700 ml. tertiary butyl alcohol
  200–250 ml. 2-propanol
  3–30 g. thiourea
  3–30 g. citric acid
  3–30 g. sodium citrate
  50–150 ml. proprionic acid
  0–250 ml. phenol.

By a preferred aspect of the present invention there is provided a composition for the single step preservation of fresh naturally coloured blooms, comprising (in amounts per liter):
  675 ml. tert-butyl alcohol
  225 ml. 2-propanol
  25 g. thiourea
  25 g. citric acid
  25 g. sodium citrate
  100 ml. propionic acid.

Tertiary butyl alcohol is an extremely efficient dehydrating agent and if used alone tends to produce brittle blooms. The effects of the tertiary butyl alcohol are modified to some extent by inclusion of 2-propanol which also lowers the freezing point of the tert-butyl alcohol.

A urea-containing compound, preferably thiourea, is an essential constituent to prevent loss of pigments from the blooms and, when used together with citric acid and sodium citrate which are also colour preservatives, it increases the efficiency of these chemicals and prolongs the active life of the composition. Although effective at relatively low concentrations the life of the composition is severely restricted for reasons described in more detail in our copending application referred to above. A higher concentration of thiourea is generally used in the present formulations than in the formulations of the copending application to compensate for the omission of many of the other, more expensive, constituents used therein.

Propionic acid and phenol are employed as pH buffers, dehydrating agents and colour stabilizers. A relatively large proportion of propionic acid is particularly effective to control the darker reds and pinks and phenol is particularly effective to control the lighter reds. A mixture of phenol and propionic acid tends to make the reds more vivid.

The process to treat the blooms according to the present invention is quite simple and straightforward. A fresh bloom is chosen and a floral wire is inserted into the stem or bloom and a weight is added to keep the bloom submerged in the composition. The composition, formulated as described hereinabove is contained in a suitable bath or container at a temperature in the range of about 45°–75° F. The bloom is left suspended in the bath for from 6 to 24 hours without any agitation, depending upon size and water content of the bloom and the freshness of the solution. Upon immersion in the composition, substantially all colour appears to disappear from the petals as dehydration occurs under the action of the dehydrating alcohols. The colour slowly returns to the normal pretreatment level as the solid colour fixers and the like take up the extracted water and actively enter solution, thus giving a useful indication of the treatment time required. Large, fleshy blooms require longer periods of immersion and care must be taken to ensure the bloom is immersed sufficiently long to treat the relatively heavy and impervious torus. Following the immersion treatment the bloom is removed from the composition and air dried at room temperature and relatively low humidity for 8 to 10 hours. Blooms thus treated can generally be stored and displayed without further treatment for relatively long periods of time (of the order of 4–6 months at least) provided the temperature and humidity conditions are suitable (i.e. up to about 80° F. and 60–70% relative humidity. More stressful environmental conditions require that the blooms be stored in sealed glass domes, where they will likely last for years or be further coated. It has been found that dipping or spraying with a conformal coating resin, such as Dow Corning R43117 Silicone Resin alone or diluted with Dow Corning Fluid 200 (Registered Trademark) (at 0.65 centistokes) or any other diluent, is satisfactory for this purpose. Preferably the coating is applied by dipping the bloom into the resin thinned with a diluent such as xylene at a temperature in the range 50°–80° F. for a few minutes. The coated bloom is then dried at room temperature for several hours to cure the resin coating. The resin cures to a clear shiny coating and leaves the bloom relatively pliable. The shiny surface is often desirable but if a matte surface is desired this can be sprayed on with any one of a number of known finishes. The thickness of the coating has a bearing on the appearance of the bloom—thin coatings lend a natural and delicate appearance to the bloom, while thick coatings make for sturdy blooms often of special beauty. After a coating treatment as described herein, roses and geraniums for example, have been exposed to light equal to several million foot-candle-hours, 95% humidity and temperatures up to 85° F. with only slight colour fading. Under more normal conditions the colours remain unaltered.

EXAMPLE 1

Samples of roses and orchids as detailed below were preserved in a solution comprising:
  675 ml. tert-butyl alcohol
  225 ml. 2-propanol
  25 g. thiourea
  25 g. citric acid
  25 g. sodium citrate
  100 ml. propionic acid.

The stems of individual blooms were wired and the blooms suspended in the preserving compositions at room temperature (45°–70° F.) for periods ranging from 6–24 hours depending on the size and water content of the bloom and the freshness of the preserving composition. In some cases it was necessary to attach a weight to the wire to ensure total immersion of the bloom in the composition. After the immersion treatment the blooms were removed from the composition and air dried at relatively low humidity (preferably less than 50%) for 8 to 10 hours. If higher humidities are encountered it may be necessary to take special steps to avoid reabsorption of water, such as be immersion in a resin such as Dow Corning R43117 ® with a solvent such as xylene. In some instances the dried blooms were subsequently coated with a coating or spray of a silicone resin at 50°–80° F. The quality of the preserved blooms was then evaluated.

| Roses | Orchids |
|---|---|
| Light Red - good | Blue - good |
| Dark Red - good | Yellow - good |
| White - good | White - good |

EXAMPLE 2

Samples of roses and orchids as in Example 1 were preserved in a solution comprising:
  600 ml. tert-butyl alcohol
  200 ml. 2-propanol
  100 ml. phenol
  100 ml. propionic acid
  25 g. citric acid
  25 g. sodium citrate
  25 g. thiourea according to the method of Example 1. The results were as follows:

| Roses | Orchids |
|---|---|
| Light Red - good | Blue - good |
| Dark Red - good | Yellow - good |
| White - good | White - good. |

We claim:

1. A water-free composition, for the single step preservation of fresh, naturally coloured blooms consisting essentially of (in amounts per liter):
  600–700 ml. tert-butyl alcohol
  200–250 ml. 2-propanol
  3–30 g. thiourea
  3–30 g. citric acid
  3–30 g. sodium citrate
  50–150 ml. propionic acid
  0–250 ml. phenol.

2. A composition as claimed in claim 1 consisting essentially of:
  675 ml. tert butyl alcohol
  225 ml. 2-propanol
  25 g. thiourea
  25 g. citric acid
  25 g. sodium citrate
  100 ml. propionic acid.

3. A composition as claimed in claim 1 consisting essentially of:
  600 ml. tert butyl alcohol
  200 ml. 2-propanol
  25 g. thiourea
  25 g. citric acid
  25 g. sodium citrate
  100 ml. propionic acid
  100 ml. phenol.

* * * * *